United States Patent [19]
Morinaga et al.

[11] 4,005,107
[45] Jan. 25, 1977

[54] 13-OXABICYCLO(10,4,0)HEXADEC-1(12)-EN-14-ONE

[75] Inventors: Tsuyoshi Morinaga; Yuji Nakazawa; Kyozo Arimoto; Katuhiko Takahashi; Yoshiyuki Arai, all of Saitama, all of Japan

[73] Assignee: Daicel, Ltd., Osaka, Japan

[22] Filed: Nov. 6, 1975

[21] Appl. No.: 629,391

[30] Foreign Application Priority Data

Nov. 11, 1974 Japan ............................. 49-129698

[52] U.S. Cl. .................. 260/343.2 R; 260/247.7 R; 260/468 K; 260/485 R; 260/514 K; 260/537 R; 260/544 R; 260/586 M; 260/610 R
[51] Int. Cl.$^2$ ........................................ C07D 311/94
[58] Field of Search ........................... 260/343.2 R

[56] References Cited

UNITED STATES PATENTS 3,778,483  12/1973  Becker et al. ................ 260/666 A Primary Examiner—Anton H. Sutto
Assistant Examiner—Jane T. Fan
Attorney, Agent, or Firm—Woodhams, Blanchard and Flynn

[57] ABSTRACT

13-Oxabicyclo(10.4.0)hexadec-1(12)-en-14-one is prepared by intramolecular cyclization of β-(2-oxocyclododecyl) propionic acid, or derivatives thereof, in the presence of an acid catalyst or a basic catalyst. The compound is an important intermediate for producing musk perfume fragrance.

3 Claims, No Drawings

13-OXABICYCLO(10,4,0)HEXADEC-1(12)-EN-14-ONE

BACKGROUND OF THE INVENTION

1. Field of the Invention

This invention relates to the compound 13-oxabicyclo(10.4.0)-hexadec-1(12)-en-14-one having the formula (1):

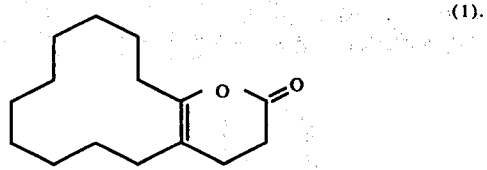

(1)

This invention relates also to a method of preparing that compound. The compound is an important intermediate for producing musk perfume fragrance ingredient.

The starting materials employable in this invention are β-(2-oxocyclododecyl)propionic acid and derivatives thereof, having the formula:

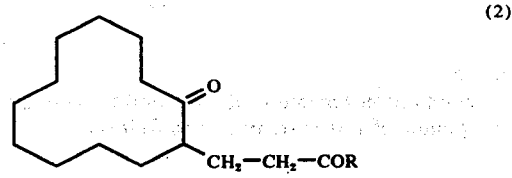

(2)

wherein R is —OH, —OCH$_3$, —OC$_2$H$_5$, —Cl, —Br,

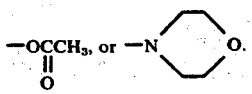

The compound β-(2-oxocyclododecyl)propionic acid, for example, can be prepared by the following steps: dehydrationcondensation of cyclododecanone and morpholine by the method described in Japenese Patent Publication No. Showa 44–60 to give 1-N-morpholino-1-cyclododecene, which is reacted with β-bromopropionic acid and then hydrolyzed. Other derivatives, such as the methyl and ethyl esters, acid chloride, acid bromide, and acetoxy derivatives are obtained from β-(2-oxocyclododecyl)propionic acid by the usual methods for transforming acids to those derivatives.

Also its morpholine amide derivative, wherein R is in formula (2), is prepared by the reaction of 1-N-morpholino-cyclododecene with β-propiolactone. The morpholine amide derivative is a novel compound.

The inventors have established a more effective method for producing β-(2-oxocyclododecyl)propionic acid by the following steps: reacting cyclododecanone with diethyl carbonate to give carbethoxycyclododecanone, reacting the carboethoxycyclododecanone with β-propiolactone in a solvent having no alkoxy group, such as benzene, toluene and ethyl ether in the presence of sodium hydride, hydrolyzing the resulting product, and then decarboxylating to give β-(2-oxocyclododecyl)propionic acid in high yield (79% based on the starting cyclododecanone theoretically).

A conventional process for preparing β-(2-oxocyclododecyl) propionic acid from 2-carbethoxycyclododecanone is disclosed in USP at No. 3,778,483. According to that patent, 2-carbethoxycyclododecanone is reacted with an acrylic ester in the presence of sodium alkoxide in an alcohol as a solvent and then the resulting intermediate is hydrolyzed to obtain β-(2-oxocyclododecyl)propionic acid. On the contrary, the foregoing process of this invention is a novel process. It does not involve any compound having an alkoxy group as a solvent, a basic substance as well as starting materials, whereby it can be effected without production of any intermediate. According to this invention, the carbethoxy group is merely removed by hydrolyzation and decarboxylation. Furthermore, the molar proportion of β-propiolactone to 2-carbethoxycyclododecanone is as low as from one to one and half. On the other hand, that of the molar proportion of methyl acrylate to 2-carbethoxycyclododecanone according to Example 19 of that patent is as high as three.

The new compound provided in this invention, namely, 13-oxabicyclo(10.4.0)haxadec-1(12)-en-14-one, is a very important intermediate for the preparation of cyclopentadecanone by the following steps as shown in the reaction schemes set forth below: (a) oxidation cleavage of the C=C bond of the formula (1) compound with ozone, (b) Wolff-Kishner reduction of the resulting 4-oxopentadecanedioic acid and esterification of the acid with methanol, (c) acyloin condensation of the dimethyl pentadecanedioate, and finally (d) reduction of the resultant acyloin. The step (c) and (d) is disclosed in Hiroo YONETANI and Masao KUBO, The Koryo, 48(1958), page 22-25 (published by Nippon Koryo Kyokai).

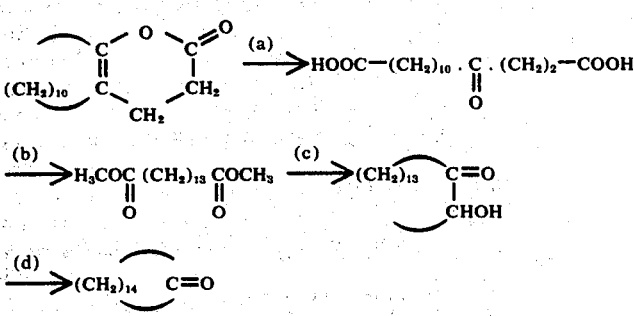

As described later in the Examples, the cyclopentadecanone was obtained from cyclododecanone through the new intermediate in this invention, 13-oxabicyclo(10.4.0)hexadec-1(12)-en-14-one in 39.7% yield (total yield based on the starting cyclododecanone).

There have been proposed many methods for producing cyclopentadecanone from many starting materials such as undecylenyl bromide, cyclododecanone, and others. The method using undecylenyl bromide as starting material, described in Indian J. Chem., 2, 355 (1964) by M. S. R. Nair et al., can produce cyclopentadecanone through 5-oxopentadecanedioic acid, which has a structure similar to 4oxopentadecanedioic acid, which latter compound is an ozone-oxidation product of 13-oxabicyclo(10.4.0)hexadec-1(12)-en-14-one, as set forth in step (a) of the reaction scheme given above. However, this method has the following disadvantages: (a) the starting material undecylenyl bromide cannot be supplied constantly, (b) the waste water treatment is troublesome because the method includes an oxidation process by potassium permanganate or chromic acid, the heavy metal of which is a nuisance to public health, and (c) the use of a Grignard reagent causes many safety troubles.

Other methods using cyclododecene as described in Japanese Patent Publication No. Showa 46-17,227 and No. Showa 49-4,459 have low yields (level of 20%). Further, the method described in Japanese Patent (unexamined) No. Showa 48-54,044 is disadvantageous for reasons of safety, because a Grignard reagent is applied in the process of this method. Thus, no method for preparing cyclopentadecanone has been provided which is fully satisfactory from all standpoints.

Contrary to these methods, the method of this invention provides a new intermediate which is useful for producing cyclopentadecanone in high yield without causing any trouble from the standpoint of safe operation and environmental pollution. Cyclopentadecanone is useful for musk perfume fragrance, which is disclosed in USP 3,778,483.

SUMMARY OF THE INVENTION

It is therefore an object of this invention to provide a new compound, 13-oxabicyclo(10.4.0)hexadec-1(12)-en-14-one and a method for preparing the same.

It is another object of this invention to provide another new compound, 15-methyl-13-oxabicyclo(10.4.0)hexadec-1(12)-en-14-one and a method for preparing the same.

It is still another object of this invention to provide yet another new compound, 16-methyl-13-oxabicyclo(10.4.0,hexadec-1(12)-en-14-one and a method for preparing the same.

According to this invention, there is provided a compound having the formula:

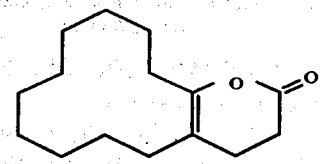

The foregoing compound is prepared by intramolecular cyclization of β-(2-oxocyclododecyl)propionic acid and derivatives thereof, having the formula:

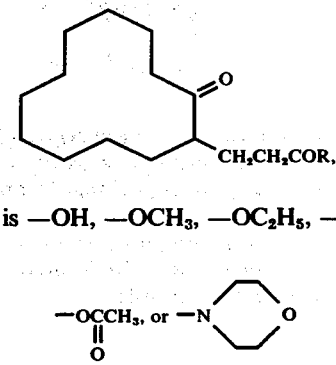

wherein R is —OH, —OCH$_3$, —OC$_2$H$_5$, —Cl, —Br,

—OCCH$_3$, or —N\_/O
  ‖
  O group.

The reaction scheme of the method for preparing the compound of this invention is as follows:

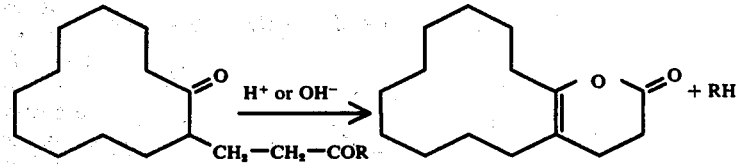

The method for preparing the new substance in this invention includes the following four methods:

I. A method of effecting intramolecular cyclization of β-(2-oxocyclododecyl)propionic acid through dehydration.

II. A method of effecting intramolecular cyclization of esters of β-(2-oxocyclododecyl)propionic acid through elimination of alcohols.

III. A method of effecting intromolecular cyclization of β-(2-oxocyclododecyl)propionic acid halide through dehydrochlorination or dehydrobromination reaction.

IV. A method of effecting intramolecular cyclization of β-(2-oxocyclododecyl)propionic acid morpholine amide through elimination of morpholine.

In more detail, the method of preparation of the new compound of this invention shall be described.

I. When β-(2-oxocyclododecyl)propionic acid is used as the starting material, an acid or a base, preferably a strong acid, is employed. The acids include mineral acids such as perchloric acid, sulfuric acid, phosphoric acid, and trifluoromethanesulfonic acid; Lewis acids such as aluminum chloride and zinc chloride; and acidic solid catalysts such as ion exchange resin, acid Fuller's earth, and silica-alumina. The bases that are useful include alkali metal salts or alkaline earth metal salts of organic acids such as sodium acetate, potassium acetate, and sodium polyacrylate.

In this case, the useful method for effecting dehydration during the intramolecular cyclization includes a heat distillation process, or a dehydration process employing a dehydrating agent. The heat distillation process includes a process wherein water is mainly distilled away by heat with a solvent of higher boiling point than that of water; or a process whereby water is distilled away as an azeotropic mixture of water and an aromatic hydrocarbon compound such as benzene, toluene, xylene, and the like.

In the dehydration process, the dehydrating agent used includes lower organic acid anhydrides, lower aliphatic acid halides, anhydrous inorganic acids, inorganic salts, molecular sieves, and silica gel; preferably acetic anhydride, acetyl chloride, polyphosphoric acid (anhydrous), cupric sulfate, calcium sulfate, and calcium chloride. The dehydration process can be effected in a solvent. Useful solvents include acids such as acetic acid and propionic acid; acid anhydrides such as acetic anhydride and propionic anhydride; esters including ethyl acetate; halogenated hydrocarbons including chloroform; ethers such as diethyl ether, diisopropyl ether, and tetrahydrofuran; and aromatic hydrocarbons such as benzene, toluene and xylene.

There are two possible ways in which the hydrogen atom can be eliminated in the method of this invention: one route is to eliminate the methyne hydrogen at position 1 of cyclododecyl group linked to the propionic residue of the β-(2-oxocyclododecyl) propionic acid and another route is to eliminate the hydrogen atom of the methylene group at position 3 as shown in the following formula:

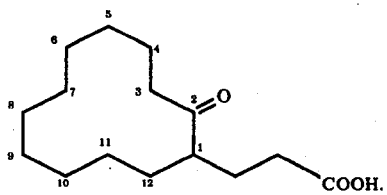

Tetrahedron Letters, 18, 1313 (1965) indicates only the route of eliminating the hydrogen atom of the methylene group at position 3 of β-(2-oxocyclohexyl)-proprionic acid as shown in the following formula:

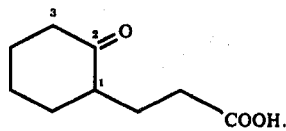

In the method for preparing the compound of this invention, however, the reaction of eliminating the methyne hydrogen at position 1 surprisingly occurs selectively to produce the new compound: 13-oxabicyclo(10.4.0)hexadec-1(12)-en-14-one.

II. The method for producing 13-oxabicyclo(10.4.0-)hexadec-1(12)-en-14-one from esters of β-(2-oxocyclododecyl) propionic acid includes two processes for elimination of alcohols: (a) heating with a solvent of higher boiling point then those of methanol and ethanol, (b) azeotropically distilling off the alcohols with benzene or toluene; in both processes, acids such as sulfonic acid, benzene sulfonic acid, and acidic ion exchange resin can be used as catalyst.

III. The method for obtaining the foregoing new compound from β-(2-oxocyclododecyl)propionic acid halide can be carried out by the following steps: reacting the β-(2-oxocyclododecyl) propionic acid with a halogenating agent such as thionyl chloride, phosphorous trichloride, and phosphorous tribromide to give β-(2-oxocyclododecyl)propionic acid halide by the usual methods; and then subjecting the product to dehydrochlorination or dehydrobromination with an aromatic amine such as pyridine and picoline or an aliphatic amine such as triethyl amine and diethyl amine.

IV. The method for producing the 13-oxabicyclo(10.4.0)hexadec-1(12)-en-14-one from β-(2-oxocyclododecyl)propionic acid morpholine amide comprises heating the starting material with an acid including benzene sulfonic acid, toluene solfonic acid, and acidic ion exchange resin as catalyst, in the presence of an organic acid, such as acetic acid and propionic acid, or its anhydride.

The reaction temperature in the method of this invention differs depending on the method for cyclization employed, but preferably is in the range of −40° to 160° C. When the dehydration cyclization method is adopted using a dehydrating agent, the reaction temperature is desirably toward the lower end of that range.

The reaction time in the method of this invention is different depending on the method for cyclization employed: in heating or distilling processes the reaction time is required to be 2 to 30 hours, but in the other processes the reaction time is from 1 to 6 hours.

13-oxabicyclo(10.4.0)hexadec-1(12)-en-14-one obtained from the reaction solution by the method in this invention can be purified by any conventional purification method. For example, the reaction solution is filtered or washed with water to remove acids and dehydrating agent and then distilled to give 13-oxabicyclo(10.4.0)hexadec-1(12)-en-14-one.

Further, the preparation method of this invention can be employed to prepare 15-methyl-13-oxabicyclo(10.4.0)hexadec-1(12)-en-14-one and 16-methyl-13-oxabicyclo(10.4.0)hexadec-1(12)-en-14-one having the general formulas:

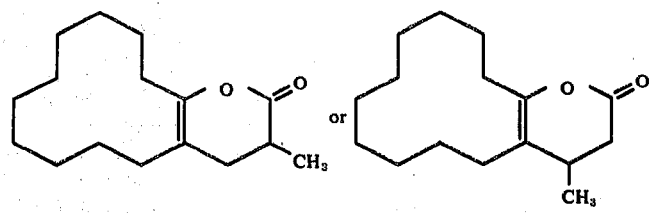

by intramolecular cyclization of the propionic acid derivatives having the following formulas:

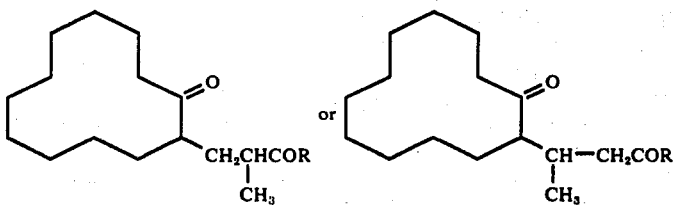

PREFERRED EMBODIMENTS OF THE INVENTION

The present invention is further described by the following illustrative Examples.

EXAMPLE 1

β-(2-oxocyclododecyl)propionic acid (8.0 g) was dissolved in a mixed solution of 400 ml of ethyl acetate, 80 ml of acetic anhydride, and 0.01 ml of 75% perchloric acid and stirred at a temperature of 15° C to 20° C for 3.5 hours. After the completion of the reaction, the resulting reaction solution was washed with 50 ml of 5% aqueous sodium bicarbonate solution, and further washed with saturated aqueous sodium chloride solution, and then dried by adding Glauber's salt (sodium sulfate) and finally filtered. Thereafter, the ethyl acetate, acetic acid and acetic anhydride in the filtrate were distilled off under reduced pressure and the resulting residue was distilled to give 6.7 g of the compound of formula (1), which was 90% of theoretical yield. The spectral data of the product were as follows:

I.R.
1760 cm$^{-1}$ (C=O)
1685 cm$^{-1}$ (C=C)
1150 – 1130 cm$^{-1}$ (—C—O)

M.S. (Mass Spectrum) parent peak (molecular weight)236 N.M.R. (Nuclear Magnetic Resonance)

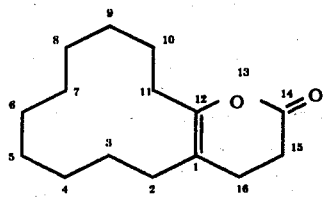

The absorption of eight hydrogen atoms at 2.7 to 1.9 ppm indicates that these atoms attach to the carbon atoms at the positions of 2, 11, 15, and 16. Also the absorption of sixteen hydrogen atoms at 1.9 to 1.0 ppm shows that these hydrogen atoms attach to the carbon atoms at the positions of 3 to 10.

If an elimination reaction of the methylene hydrogen on the carbon at the position 3 of the cyclododecyl group of the starting material, β-(2-oxocyclododecyl)-propionic acid, had occurred to produce a compound having a double bond between the carbon atoms at the positions 11 and 12, which is represented by the formula:

the hydrogen atom attached to the carbon at position 11 should show an absorption in low magnetic field because it acts as an olefinic proton. However no equivalent peak is present in the N.M.R. of the compound prepared as described above. From this, it is concluded that the prepared compound has the formula (1).

Elementary Analysis
theoretical value (%)C = 76.27, H = 10.58,
experimental value (%)C = 76.22, H = 10.23.

EXAMPLE 2

Into a reactor were placed 6.47 parts of β-(2-oxocyclododecyl)propionic acid, 0.32 part of anhydrous paratoluene sulfonic acid, and 150 parts of anhydrous xylene. The solution was refluxed by heating to remove continuously the water produced by enol-form lactonization of β-(2-oxocyclododecyl)propionic acid. The resulting solution was treated in the same manner as the Example 1 to obtain 3.03 parts of the product of formula (1) which was 50.3% in yield.

EXAMPLE 3

Into a reactor were placed 10 parts of β-(2-oxocyclododecyl)propionic acid, 10 parts of acetic anhydride, 30 parts of anhydrous diethyl ether, 2 parts of ion exchange resin (Amberlyst 15, a product of Rohm and Haas Co.). The solution was heated for 6 hours under reflux of anhydrous diethyl ether. After completion of heating, the reaction solution was cooled and the catalyst was filtered off, and then low boiling materials were distilled off under reduced pressure. Further, 7.02 parts of the product of formula (1) was obtained by distillation under reduced pressure. The yield of the product was 75.5%.

EXAMPLE 4

Ten parts of β-(2-oxocyclododecyl)propionic acid, 11 parts of acetyl chloride, 50 parts of anhydrous ethyl ether, and 2 parts of Amberlyst 15 were stirred at 0° C for 6 hours.

Thereafter, the solution was treated by the same method as described in Example 3 to give 7.25 parts of the compound of formula (1) in 78.1% yield.

EXAMPLE 5

Ten parts of β-(2-oxocyclododecyl)propionic acid, 10 parts of acetic anhydride, 85 parts of acetic acid, and 2 parts of Amberlyst 15 were stirred at 10° C for 6 hours.

Then, the solution was treated by the same method as described in Example 3 to give 7.12 parts of the compound of formula (1) in 76.6% yield.

EXAMPLE 6

Five parts of β-(2-oxocyclododecyl)propionic acid, 5 parts of acetic acid, 35 parts of anhydrous diethyl ether, and 0.1 part of trifluoromethanesulfonic acid were stirred at 0° C for 6 hours.

Then, the solution was treated by the same method as described in Example 1 to give 3.37 parts of the compound of formula (1) in 72.5% yield.

EXAMPLE 7

Ten parts of β-(2-oxocyclododecyl)propionic acid, 80 parts of acetic anhydride, and 2 parts of Amberlyst 15 were stirred at 0° C for 6 hours.

Then, the solution was treated in the same manner as described in Example 3 to give 8.05 parts of the compound of formula (1) in 86.6% yield.

EXAMPLE 8

Ten parts of β-(2-oxocyclododecyl)propionic -oxocyclododecyl)propionic acid, 10 parts of acetic anhydride, 60 parts of benzene, and 1 part of sulfuric acid were stirred at a temperature of 5° to 10° C for 6 hours.

The solution was treated in the same manner as described in Example 1 to give 5.45 parts of the compound of formula (1) in 58.7% yield.

EXAMPLE 9

Five parts of β-(2-oxocyclododecyl)propionic acid, 5 parts of acetic anhydride, 20 parts of benzene, and 1 part of aluminum chloride were stirred at 30° C for 8 hours.

Then, insoluble matter was filtered off and the filtrate was washed with water, and the benzene layer was dried with Glauber's salt. The resultant solution was treated by the same method as described in Example 1 to give 2.03 parts of the compound of formula (1) in 43.7% yield.

EXAMPLE 10

Five parts of β-(2-oxocyclododecyl)propionic acid, 0.05 part of anhydrous sodium acetate made from sodium acetate trihydrate by heating at 120° C for 8 hours, and 25 parts of acetic anhydride were reacted under reflux for 6 hours.

Into the reaction solution was added benzene, the insoluble matters in the solution were filtered off and the filtrate was treated in the same manner as described in Example 1 to obtain 1 part of distillate which was confirmed to be the object compound, 13-oxabicyclo(10.4.0)hexadec-1(12)-en-14-one, by gas chromatography in 24% yield.

EXAMPLE 11

Five parts of β-(2-oxocyclododecyl)propionic acid, 0.05 part of sodium polyacrylate (ARONBIS GX produced in NIPPON JUNYAKU Co., Ltd.), and 25 parts of acetic anhydride were reacted for 9.5 hours under reflux. After completion of the reaction, the insoluble matter in the foregoing solution was filtered off and then the filtrate was treated by the same method as described in Example 1 to give 2.6 parts of distillate which was the object compound: 13-oxabicyclo(10.4.0)hexadec-1(12)-en-14-one. The compound was confirmed by gas chromatography in 23.5% yield.

EXAMPLE 12

Thirty parts of β-(2-oxocyclododecyl)propionic acid, 60 parts of acetic anhydride, 300 parts of acetic acid, and 6 parts of Amberlyst 15 were placed into a reactor and stirred at a temperature of 5° C to 10° C for 4 hours.

The reaction solution was treated in the same manner as described in Example 3 to give 25.94 parts of the compound of formula (1) in 93.06% yield.

EXAMPLE 13

β-(2-oxocyclododecyl)propionic acid was esterified by the usual method to give methyl β-(2-oxocyclododecyl)propionate. Five parts of the ester, 0.5 parts of paratoluene sulfonic acid, and 60 parts of mixed xylene were placed into a reactor and reacted for 30 hours under heat reflux.

After cooling, the reaction solution was treated in the same manner as described in Example 1 to give 4.5 parts of distillate. The infrared spectrum of the product indicated characteristic absorptions peculiar to 13-oxabicyclo(10.4.0)hexadec-1(12)-en-14-one at 1760 $cm^{-1}$, 1685 $cm^{-1}$, and 1150 $cm^{-1}$.

EXAMPLE 14

Ten parts of β-(2-oxocyclododecyl)propionic acid, 6 parts of thionyl chloride, and 35 parts of anhydrous benzene were placed into a reactor and allowed to stand at 0° C for 3 hours and further at room temperature overnight. Then, the excess amount of thionyl chloride and the benzene were distilled off under reduced pressure to give β-(2-oxocyclododecyl)propionic acid chloride. The acid chloride was dissolved in 25 parts of benzene. Into the resulting solution was added dropwise 35 parts of benzene solution containing 30 wt.% pyridine and the mixture was stirred for 6 hours. The produced crystals were filtered off. The filtrate was washed with dilute hydrochloric acid to remove excess pyridine, the organic layer was washed to remove the hydrochloric acid, and then dried with Glauber's salt. Thereafter the resulting solution was treated by the same method as in Example 1 to give 6.3 parts of 13-oxabicyclo(10.4.0)-hexadec-1(12)-en-14-one in 68.4% yield.

EXAMPLE 15

1-N-morpholino-1-cyclododecene (82.9 parts) obtained by the method in Japanese Patent Publication No. Showa 45-16,970 was allowed to react with 19.8 parts of β-propiolactone in 25 parts of chlorobenzene solution at 160° C under dry nitrogen atmosphere for 6 hours. Then the chlorobenzene and unreacted 1-N-morpholino-1-cyclododecene were distilled off under reduced pressure. The residual solution was continued to be distilled, thus obtaining 63.6 parts of β-(2-oxocyclododecyl)propionic acid morpholine amide in 71.6% yield based on the β-propiolactone. The boiling point of the product was 184°–186° C/0.3 mm Hg. Its infrared absorption spectrum showed the absorption of C = O of the cyclic ketone at 1700 $cm^{-1}$, the absorption of C = O of the acid amide at 1645 $cm^{-1}$, the absorption of C — N on the morpholine residue at 1230 cm$^{-1}$, and the absorption of C — O on the morpholine residue at 1117 cm$^{-1}$.

Mass Spectrum parent peak 323
Nuclear Magnetic Resonance indicated
the absorption of 14 hydrogen atoms at 1.0 to 1.5 ppm,
the absorption of 11 hydrogen atoms at 1.5 to 3.1 ppm, and the absorption of 8 hydrogen atoms at 3.3 to 3.9 ppm.

Elementary Analysis $C_{19}H_{33}NO_3$
theoretical value (%)C = 70.65, H = 10.30, N = 4.34
determined value (%)C = 70.71, H = 10.38, N = 4.30.

Five parts of the foregoing β-(2-oxocyclododecyl)-propionic acid morpholine amide, 0.2 part of paratoluene sulfonic acid, 50 parts of acetic acid, and 5 parts of acetic anhydride were refluxed for 36 hours. And then 300 parts of benzene was added into the solution and washed with aqueous sodium bicarbonate to remove the catalyst and acetic acid. Thereafter, the resulting solution was treated by the same method as described in Example 1 to give 1.54 parts of 13-oxabicyclo(10.4.0)hexadec-1(12)-en-14-one in 32.8% yield.

EXAMPLE 16

One part of β-(2-oxocyclododecyl)propionic acid, 1 part of acetic anhydride, 10 parts of glacial acetic acid, and 0.5 part of Amberlyst 15 were allowed to react at 50° C for 4 hours and the reaction solution was withdrawn and analyzed by gas chromatography to find that β-(2-oxocyclododecyl)propionic acid was not present and 13-oxabicyclo(10.4.0)hexadec-1(12)-en-14-one was produced in 99% selectivity.

EXAMPLE 17

Into a column of 1.6 mm diameter was packed Amberlyst 15 and a solution composed of β-(2-oxocyclododecyl)propionic acid, acetic anhydride, and glacial acetic acid in the ratio of 1:1:10 parts by weight was flowed down through the column at a residence time of 5 hours. The effluent was fractionally cut each hour and each fraction was analyzed by gas chromatography. The gas chromatogram of the reaction solution after 5 hours from outset of the flow-down showed that β-(2-oxocyclododecyl)-propionic acid was not present and 13-oxabicyclo(10.4.0)hexadec-1(12)-en-14-one was produced in 99% yield.

Reference Example 1

Cyclododecanone and diethyl carbonate were allowed to react in the presence of a base to give 2-carboethoxycyclododecanone in 93% yield. Ten grams of the 2-carboethoxycyclododecanone was dissolved in 40 ml of toluene and the resulting solution was added dropwise into a solution of 2.4 g of sodium hydride (purity 60%) suspended in toluene and kept at 80° C. After the completion of the dropping, the solution thus obtained was stirred for 30 minutes and then the reaction temperature was cooled to room temperature. Thereafter, into the solution was dropped 5.7 g of β-propiolactone and further 25 ml of aqueous sodium hydroxide solution was added, and was refluxed for 4 hours. After the reaction was complete, the aqueous layer of the solution was drawn off and acidified with hydrochloric acid to give 8.5 g of β-(2-oxocyclododecyl)propionic acid as white crystals. The product melts at 101° to 102° C.

Reference Example 2

Six grams of 13-oxabicyclo(10.4.0)hexadec-1(12)-en-14-one was dissolved in 100 ml of chloroform and oxygen containing about 5% of ozone was bubbled into the solution at the rate of 300 ml/min. at −20° C for 3 hours. The reaction temperature was raised to room temperature and the oxygen within the reactor was purged with nitrogen. Then 10 g of triphenyl phoshine was added and stirred for 1 hour. After the chloroform in the reactor solution was distilled off, the residue was dissolved in 50 ml of methonal, 30 ml of 5% NaOH aqueous solution was added and heated at 80° C for 3 hours, and finally acidified with hydrochloric acid, thus obtaining 7.3 g of 4-oxopentadecanedioic acid in 90% yield. The product melts at 117° to 118° C.

Reference Example 3

Five grams of 4-oxopentadecanedioic acid obtained in Reference Example 2 and 2.2 g of potassium hydroxide were dissolved in 40 ml of ethylene glycol, 12 ml of hydrazine hydrate was added and the mixture was refluxed for 8 hours. Then, 7.2 g of potassium hydroxide was added to the mixture and the mixture was heated for 6 hours. The reaction solution was poured into water and acidified with concentrated hydrochloric acid to give a precipitate, which was esterified with methanol and distilled off at 130° to 131° C/0.1 mm Hg, thus obtaining 4.2 g of the compound: dimethyl pentadecane dicarboxylate in 80% yield.

The latter compound could be transformed to cyclopentadecanone in 75% yield by the general method of acyloin condensation and reduction.

Thus, still further, the total yield of cyclopentadecene from 2-carboethoxy cyclodecanone was 39.7% by the four steps based on the Examples: Reference Example 1 → Example 12 → Reference Example 2 → Reference Example 3.

The embodiments of the invention in which an exclusive property or privilege is claimed are defined as follows:

1. A compound having the formula:

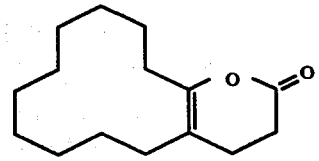

2. A compound having the formula:

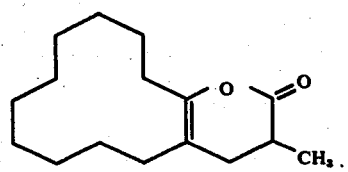

3. A compound having the formula:

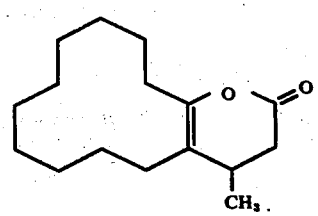

* * * * *